(12) United States Patent
Druzgala et al.

(10) Patent No.: US 6,552,046 B2
(45) Date of Patent: Apr. 22, 2003

(54) MATERIALS AND METHODS FOR THE TREATMENT OF GASTROESOPHAGEAL REFLUX DISEASE

(75) Inventors: Pascal Druzgala, Santa Rosa, CA (US); Peter G. Milner, Los Altos Hills, CA (US); Jürg Pfister, Los Altos, CA (US); Cyrus Becker, Menlo Park, CA (US)

(73) Assignee: Aryx Therapeutics, Sunnyvale, CA (US)

(*) Notice: Subject to any disclaimer, the term of this patent is extended or adjusted under 35 U.S.C. 154(b) by 0 days.

(21) Appl. No.: 09/876,698

(22) Filed: Jun. 7, 2001

(65) Prior Publication Data

US 2002/0025970 A1 Feb. 28, 2002

Related U.S. Application Data

(60) Provisional application No. 60/209,926, filed on Jun. 7, 2000.

(51) Int. Cl.$^7$ .................. A61K 31/445; C07D 211/56
(52) U.S. Cl. .............. 514/329; 514/318; 514/319; 546/191; 546/193; 546/194; 546/195; 546/205; 546/224
(58) Field of Search ............... 514/318, 319, 514/329; 546/191, 193, 194, 195, 205, 224

(56) References Cited

U.S. PATENT DOCUMENTS

| 4,962,115 | A | 10/1990 | Van Daele | 514/318 |
|---|---|---|---|---|
| 5,057,525 | A | 10/1991 | Van Daele | 514/318 |
| 5,395,832 | A | 3/1995 | Ito et al. | |
| 5,500,422 | A | 3/1996 | Ito et al. | |

FOREIGN PATENT DOCUMENTS

| DE | 199 33 926 A | 1/2001 |
|---|---|---|
| EP | 0076530 | 9/1982 |
| EP | 0 640 601 B1 | 12/1996 |
| EP | 1 149 832 A1 | 10/2001 |
| JP | 11292846 | 10/1999 |
| WO | 99/02496 | * 1/1999 |

OTHER PUBLICATIONS

Barnes, N.M., B. Costall, R.J. Naylor, F.D. Tattersall (Apr. 5, 1998) "Identification of 5–$HT_3$ recognition sites in the ferret area postrema" *J. Pharm. Pharmacol.* 40:586–588.

Decktor, Dennis, Robert G. Pendleton, Anne T. Elnitsky, Ann M. Jenkins, Anthony P. McDowell (1988) "Effect of metoclopramide, bethanechol and the cholecystokinin receptor antagonist, L–364,718, on gastric emptying in the rat" *European Journal of Pharmacology* 147:313–316.

Stacher, Georg, Gabriele Gaupmann, Gerda Mittelbach, Christa Schneider, Hermann Steinringer, Brigitte Langer (Nov. 1987) "Effects of Oral Cisapride on Interdigestive jejunal Motor Activity, Psychomotor Function, and Side–Effect Profile in Healthy Man" *Digestive Diseases and Sciences* 32(11):1223–1230.

Van Daele, Georges H.P., Marcel F.L. De Bruyn, Francois M. Sommen et al. (1986) "Synthesis of Cisapride, a Gastrointestinal Stimulant Derived From Cis–4–Amino–3–Methoxypiperidine" *Drug Development Research* 8:225–232.

* cited by examiner

*Primary Examiner*—Ceila Chang
(74) *Attorney, Agent, or Firm*—Saliwanchik, Lloyd & Saliwanchik

(57) ABSTRACT

The subject invention provides novel compounds and compositions for the safe and effective treatment of gastroesophageal reflux and related conditions. In a preferred embodiment, the compositions of the subject invention comprise esterified cisapride derivatives. These compositions possess potent activity in treating gastroesophageal reflux disease and substantially reduce adverse effects associated with the administration of cisapride. These adverse effects include, but are not limited to, diarrhea, abdominal cramping and elevations of blood pressure and heart rate.

33 Claims, No Drawings

MATERIALS AND METHODS FOR THE TREATMENT OF GASTROESOPHAGEAL REFLUX DISEASE

CROSS-REFERENCE TO RELATED APPLICATION

The subject application claims priority to provisional application U.S. Ser. No. 60/209,926, filed Jun. 7, 2000.

BACKGROUND OF INVENTION

Cisapride is one of a class of compounds known as benzamide derivatives, the parent compound of which is metoclopramide. U.S. Pat. Nos. 4,962,115 and 5,057,525 (collectively "Van Daele" and incorporated by reference in their entireties) disclose N-(3-hydroxy-4-piperidenyl) benzamides of cisapride. Van Daele discloses that these compounds, the pharmaceutically acceptable acid addition salts thereof and the stereochemically isomeric forms thereof, stimulate the motility of the gastrointestinal system.

As a class, these benzamide derivatives have several prominent pharmacological actions. The prominent pharmacological activities of the benzamide derivatives are due to their effects on the neuronal systems which are modulated by the neurotransmitter serotonin. The role of serotonin, and thus the pharmacology of the benzamide derivatives, has been broadly implicated in a variety of conditions for many years. Thus, research has focused on locating the production and storage sites of serotonin as well as the location of serotonin receptors in the human body in order to determine the connection between these sites and various disease states or conditions.

In this regard, it was discovered that a major site of production and storage of serotonin is the enterochromaffin cell of the gastrointestinal mucosa. It was also discovered that serotonin has a powerful stimulating action on intestinal motility by stimulating intestinal smooth muscle, speeding intestinal transit, and decreasing absorption time, as in diarrhea. This stimulating action is also associated with nausea and vomiting.

Because of their modulation of the serotonin neuronal system in the gastrointestinal tract, many of the benzamide derivatives are effective anti-emetic agents and are commonly used to control vomiting during cancer chemotherapy or radiotherapy, especially when highly emetogenic compounds such as cisplatin are used. This action is almost certainly the result of the ability of the compounds to block the actions of serotonin (5HT) at specific sites of action, called the 5HT3-receptor, which was classically designated in the scientific literature as the serotonin M-receptor. Chemotherapy and radiation therapy may induce nausea and vomiting by the release of serotonin from damaged enterochromaffin cells in the gastrointestinal tract. Release of the neurotransmitter serotonin stimulates both afferent vagal nerve fibers (thus initiating the vomiting reflex) and serotonin receptors in the chemoreceptor trigger zone of the area postrema region of the brain. The anatomical site for this action of the benzamide derivatives, and whether such action is central (CNS), peripheral, or a combination thereof, remains unresolved (Barnes et al., J. Pharm. Pharmacol. 40: 586–588, 1988). Cisapride, like the other benzamide derivatives would appear to be an effective anti-emetic agent based on its ability to modulate the activity of serotonin at the 5HT3 receptor.

A second prominent action of the benzamide derivatives is in augmenting gastrointestinal smooth muscle activity from the esophagus through the proximal small bowel, thus accelerating esophageal and small intestinal transit as well as facilitating gastric emptying and increasing lower esophageal sphincter tone (Decktor et al., Eur. J. Pharmacol. 147: 313–316, 1988). Although the benzamide derivatives are not cholinergic receptor agonists per se, the aforementioned smooth muscle effects may be blocked by muscarinic receptor blocking agents such as atropine or neuronal transmission inhibitors of the tetrodotoxin type which affect sodium channels. Similar blocking activity has been reported for the contractile effects of serotonin in the small intestine. It is currently believed that the primary smooth muscle effects of the benzamide derivatives are the result of an agonist action upon a new class of serotonin receptors referred to as 5HT4 receptors which are located on interneurons in the myenteric plexus of the gut wall. Activation of these receptors subsequently enhances the release of acetylcholine from parasympathetic nerve terminals located near surrounding smooth muscle fibers, and it is the combination of acetylcholine with its receptors on smooth muscle membranes which is the actual trigger for muscle contraction.

Cisapride is presently used primarily to treat gastroesophageal reflux disease. This disease is characterized as the backward flow of the stomach contents into the esophagus. One of the most important factors in the pathogenesis of gastroesophageal reflux disease is a reduction in the pressure barrier due to the failure of the lower esophageal sphincter. Failure of the lower esophageal sphincter can arise due to a low basal pressure, sphincter relaxation, or to a non-compensated increase in intragastric pressure. Other factors in the pathogenesis of the disease are delayed gastric emptying, insufficient esophageal clearing due to impaired peristalsis and the corrosive nature of the reflux material which can damage esophageal mucosa. Cisapride is thought to strengthen the anti-reflux barrier and improve esophageal clearance by increasing the lower esophageal sphincter pressure and enhancing peristaltic contractions.

Because of its activity as a prokinetic agent, cisapride would also appear to be useful to treat dyspepsia, gastroparesis, constipation, post-operative ileus, and intestinal pseudo-obstruction. Dyspepsia is a condition characterized by an impairment of the power or function of digestion that can arise as a symptom of a primary gastrointestinal dysfunction or as a complication due to other disorders such as appendicitis, gallbladder disturbances, or malnutrition. Gastroparesis is a paralysis of the stomach brought about by a motor abnormality in the stomach or as a complication of diseases such as diabetes, progressive systemic sclerosis, anorexia nervosa or myotonic dystrophy. Constipation is a condition characterized by infrequent or difficult evacuation of feces resulting from conditions such as lack of intestinal muscle tone or intestinal spasticity. Post-operative ileus is an obstruction in the intestine due to a disruption in muscle tone following surgery. Intestinal pseudo-obstruction is a condition characterized by constipation, colicky pain, and vomiting, but without evidence of physical obstruction.

Drug toxicity is an important consideration in the treatment of humans and animals. Toxic side effects (adverse effects) resulting from the administration of drugs include a variety of conditions which range from low grade fever to death. Drug therapy is justified only when the benefits of the treatment protocol outweigh the potential risks associated with the treatment. The factors balanced by the practitioner include the qualitative and quantitative impact of the drug to be used as well as the resulting outcome if the drug is not provided to the individual. Other factors considered include the physical condition of the patient, the disease stage and its history of progression, and any known adverse effects associated with a drug.

Drug elimination is typically the result of metabolic activity upon the drug and the subsequent excretion of the drug from the body. Metabolic activity can take place within the vascular supply and/or within cellular compartments or organs. The liver is a principal site of drug metabolism. The metabolic process can be categorized into synthetic and nonsynthetic reactions. In nonsynthetic reactions, the drug is chemically altered by oxidation, reduction, hydrolysis, or any combination of the aforementioned processes. These processes are collectively referred to as Phase I reactions.

In Phase II reactions, also known as synthetic reactions or conjugations, the parent drug, or intermediate metabolites thereof, are combined with endogenous substrates to yield an addition or conjugation product. Metabolites formed in synthetic reactions are, typically, more polar and biologically inactive. As a result, these metabolites are more easily excreted via the kidneys (in urine) or the liver (in bile). Synthetic reactions include glucuronidation, amino acid conjugation, acetylation, sulfoconjugation, and methylation.

More than 90% of a dose of cisapride is metabolized by oxidative N-dealkylation at the piperidine nitrogen or by aromatic hydroxylation occurring on either the 4-fluorophenoxy or benzamide rings.

The administration of cisapride to a human has been found to cause adverse effects including, CNS disorders, increased systolic pressure, interactions with other drugs, diarrhea, and abdominal cramping. Further, it has been reported that intravenous administration of cisapride demonstrates the occurrence of additional adverse (side) effects not experienced after oral administration of cisapride (Stacher et al. [1987] Digestive Diseases and Sciences 32(11):1223–1230). It is believed that these side effects are caused by the metabolites which result from the oxidative dealkylation or aromatic hydroxylation of the compound which occurs in the cytochrome P-450 detoxification system.

Between July 1993 and December 1999, cisapride (PROPULSID, Janssen Pharmaceutica Products, L.P.) has been reportedly associated with at least 341 serious cardiac arrhythmias. These arrhythmias include ventricular tachycardia, ventricular fibrillation, torsades de pointes, and QT prolongation. Eighty (80) deaths have been reported. As a result of these adverse effects, the product is being voluntarily withdrawn from the open market (in the United States) on Jul. 14, 2000; however, the drug will be available through an investigational limited access program.

Thus, it would be particularly desirable to provide compounds with the therapeutic advantages of cisapride which would not have the aforementioned disadvantages.

BRIEF SUMMARY

The subject invention provides novel compounds and compositions for the safe and effective treatment of gastroesophageal reflux and related conditions. In a preferred embodiment, the compositions of the subject invention comprise esterified cisapride derivatives. These compositions possess potent activity in treating gastroesophageal reflux disease and substantially reduce adverse effects associated with the administration of cisapride. These adverse effects include, but are not limited to, diarrhea, abdominal cramping and elevations of blood pressure and heart rate.

Additionally, the novel compositions of the subject invention are useful in treating emesis and other conditions, including but not limited to dyspepsia, gastroparesis, constipation, and intestinal pseudo-obstruction. As an added benefit, adverse effects associated with the administration of cisapride are also reduced in these methods of treatment.

Advantageously, the subject invention provides compounds which are readily metabolized by the physiological metabolic drug detoxification systems. Specifically, in a preferred embodiment, the therapeutic compounds of the subject invention contain a moiety, which does not detract from the ability of these compounds to provide a therapeutic benefit, but which makes these compounds more susceptible to degradation by hydrolases. Specifically exemplified are compounds which contain an ester group making them susceptible to degradation by serum and/or cytosolic esterases, thereby avoiding the cytochrome P-450 drug detoxification system associated with adverse effects caused by cisapride and reducing the incidence of adverse events.

The subject invention further provides methods of treatment comprising the administration of these compounds to individuals in need of treatment for gastroesophageal reflux disease and related conditions.

Advantageously, the therapeutic compounds of the subject invention are stable in storage and provide for safer metabolism of the drugs as compared to other drugs which are available for treatment of gastroesophageal reflux, dyspepsia, gastroparesis, constipation, post-operative ileus, and intestinal pseudo-obstruction; therefore, the compounds of the subject invention can be used with a lower incidence of side effects and toxicity.

In a further embodiment, the subject invention pertains to the breakdown products which are formed when the therapeutic compounds of the subject invention are acted upon by hydrolases. These breakdown products can be used as described herein to monitor the clearance of the therapeutic compounds from a patient.

In yet a further embodiment, the subject invention provides methods for synthesizing the therapeutic compounds of the subject invention.

DETAILED DISCLOSURE

The subject invention provides novel compounds which are more easily metabolized by the metabolic drug detoxification systems. This invention is also drawn to methods of treating disorders, such as gastroesophageal reflux disease, and related conditions. Specifically, the subject invention provides analogs of cisapride which have been designed to be more susceptible to degradation by hydrolases, particularly serum and/or cytosolic esterases and methods of treatment comprising the administration of these analogs to individuals.

Advantageously, the therapeutic compounds of the subject invention are stable in storage but have a relatively short half-life in the physiological environment; therefore, the compounds of the subject invention can be used with a lower incidence of side effects and toxicity.

In a preferred embodiment of the subject invention, therapeutic compounds are provided which are useful in the treatment of gastroesophageal reflux disease and which contain a moiety, such as an ester group, which is susceptible to degradation by hydrolases, thereby breaking down the compound and facilitating its efficient removal from the treated individual. In a preferred embodiment, the therapeutic compounds are metabolized by the Phase I drug detoxification system.

A further aspect of the subject invention pertains to the breakdown products which are produced when the therapeutic compounds of the subject invention are acted upon by a hydrolase. The presence of these breakdown products in the urine or serum can be used to monitor the rate of clearance of the therapeutic compound from a patient.

Degradation of the compounds of the subject invention by enzymes such as hydrolases (esterases, peptidases, lipases, glycosidases, phosphateases, etc.) is particularly advantageous for drug metabolism because these enzymes are ubiquitously distributed and their activity is not dependent on age, gender, or disease state to the same extent as oxidative hepatic drug metabolism.

The subject invention further provides methods of treating disorders, such as gastroesophageal reflux disease comprising the administration of a therapeutically effective amount of cisapride analogs to an individual in need of treatment. In a specific embodiment, the subject invention provides esterified cisapride analogs and pharmaceutical compositions of these esterified compounds.

The subject invention further provides materials and methods for the treatment of emesis and such other conditions, including but not limited to dyspepsia, gastroparesis, constipation, and intestinal pseudo-obstruction, while substantially reducing adverse effects associated with the administration of cisapride.

In a preferred embodiment of the subject invention, therapeutic compounds are provided which are useful in the treatment of gastroesophageal reflux, dyspepsia, gastroparesis, constipation, post-operative ileus, and intestinal pseudo-obstruction and which contain an ester group which is acted upon by esterases thereby breaking down the compound and facilitating its efficient removal from the treated individual.

The subject invention further provides methods of synthesizing the unique and advantageous therapeutic compounds of the subject invention. Particularly, methods of producing less toxic therapeutic agents comprising introducing ester groups into therapeutic agents (target drugs) are taught. The ester linkage may be introduced into the compound at a site which is convenient in the manufacturing process for the target drug. Additionally, the sensitivity of the ester linkage may be manipulated by the addition of side groups which hinder or promote the hydrolytic activity of the hydrolases or esterases responsible for cleaving the drug at the ester locus. Methods of adding such side groups, as well as the side groups themselves, are well known to the skilled artisan and can be readily carried out utilizing the guidance provided herein.

The chemical synthesis of the disclosed analogs of cisapride can be performed by the method described in European Patent Application No. 0,076,530 A2 published Apr. 13, 1983, U.S. Pat. Nos. 4,962,115 and 5,057,525 and in Van Daele et al., Drug Development Res. 8: 225–232 (1986), the disclosures of which are incorporated herein by reference in their entireties, and modified by the incorporation of an ester group at a point convenient in the synthesis of the disclosed compounds. Exemplary, non-limiting synthesis schemes for certain esterified cisapride analogs of the subject invention are provided below.

The present invention is concerned with novel N-(4-piperidinyl)benzamides having the general Formula (I) and their pharmaceutically acceptable salts.

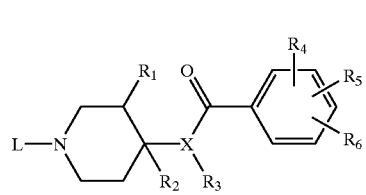

(I)

Wherein:
R$_1$ is H, C$_{1-4}$ alkyl, OH, OC$_{1-4}$alkyl, —COOH, —COOC$_{1-4}$alkyl, —O(C=O)OC$_{1-4}$alkyl, —O(C=O)C$_{1-4}$alkyl, or —C$_{1-4}$alkylNR$_7$R$_8$ where R$_7$ and R$_8$ are, independently, H or C$_{1-4}$ alkyl;

R$_2$ is H, C$_{1-4}$ alkyl, —OC$_{1-4}$alkyl, —COOH, or —(C=O)OC$_{1-4}$alkyl;

X is O or N;

R$_1$ and X are in the cis- or trans-configuration;

R$_3$ is H or C$_{1-3}$ alkyl (if X is an oxygen atom, then R$_3$ does not exist);

R$_4$, R$_5$, and R$_6$ are each, independently, selected from the group consisting of hydrogen, C$_{1-4}$ alkyl, —OC$_{1-4}$ alkyl, halogen atom, hydroxy, cyano, nitro, amino, mono- and di(lower alkyl)amino, aminocarbonyl, arylcarbonylamino, alkylcarbonylamino, lower-alkyl carbonyl, lower-alkyl carbonyloxy, aminosulfonyl, lower-alkylsulfinyl, lower-alkylsulfonyl, lower-alkylthio and mercapto; and wherein L has the formula —C$_n$H$_{2n}$—X—C$_m$H$_{2m}$—(CR$_9$R$_{10}$)$_p$—(C=O)O—Y, wherein n is an integer from 1 to 4 inclusive;

X is —CH(OH)—, —NH—, —S—, —O—, or a direct bond;

m is an integer from 0 to 4 inclusive;

p is 0 or 1;

R$_9$ and R$_{10}$ are, independently, H, C$_{1-4}$ alkyl, or R$_9$R$_{10}$ are linked and together form a 5-or a 6-membered cycloalkyl ring; and Y is H, C$_{1-14}$ alkyl or cycloalkyl optionally substituted by 1 or more (2 to 8) heteroatoms selected from the group consisting of O; N; S; or aryl or heteroaryl optionally substituted by 1 or more (2 to 8) halogen atoms, C$_{1-4}$ alkyl, C$_{1-4}$alkoxy, hydroxy, cyano, amino, alkylamino, dialkylamino, trifluoromethyl, —COOH, or —COOC$_{1-4}$ alkyl (when Y is hydrogen, the compounds can also be quaternary ammonium complexes such as tetrabutyl or tetraethylammonium and trigonellinium).

Those skilled in the art will recognize that the structure of Formula I has at least 2 asymmetric centers at the 3- and 4-positions of the piperidine ring (carbon atoms bearing the R$_1$ and R$_2$ groups). Substituents on the piperidinyl ring can have the cis- or the trans-configuration. Accordingly, the subject invention includes the 4 individual enantiomers associated with these 2 carbon centers, namely the 3R,4R; 3S,4S; 3R,4S; and 3S,4R conformations.

Preferred compounds are those wherein R$_4$, R$_5$, and R$_6$ are, independently, selected from the group consisting of halo, amino, mono- and dialkylamino, and lower alkyloxy.

Particularly preferred compounds are those wherein R$_4$ is methoxy, R$_5$ is amino or methylamino, and R$_5$ is chloro, in the 2-, 4-, and 5-position of the phenyl ring, respectively.

Particularly, preferred compounds of the subject invention include those where: R$_1$=OCH$_3$, R$_2$=H; X=O or N (if X=N, then R$_3$=H); R$_4$, R$_5$, and R$_6$ are methoxy, amino, and chlorine at the 2, 4, and 5-position of the phenyl ring, respectively. $R_1$ and X are in the cis-configuration.

Preferred compounds within the scope of this invention have the cis-configuration.

Particularly preferred compounds of this invention have the following formulae:

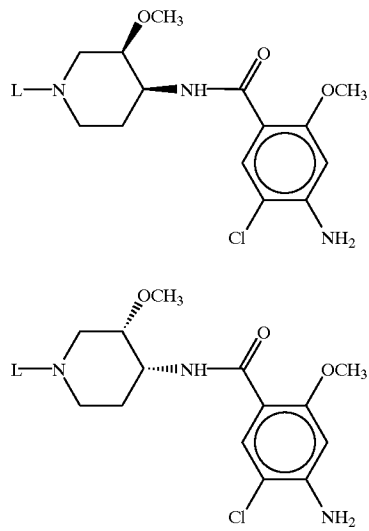

where IIIa and IIIb are mirror images of each other (enantiomers), and where L is defined as shown in Formula (II):

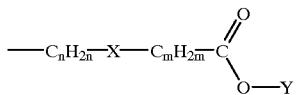

where n=1 to 4, m=0 to 4, X is a direct bond and Y is hydrogen, lower alkyl, or substituted aryl.

In the most preferred compounds, n=2, m=0, X is a direct bond, and Y is hydrogen, methyl, ethyl, isopropyl, sec-butyl, or 4-fluorophenyl.

The compounds of Formula I can generally be prepared by the reaction of an amine of Formula (IV) with a carboxylic acid of Formula (V).

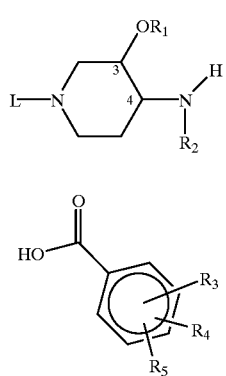

Functional derivatives of the carboxylic acids shown as Formula (V) can also be used, as would be known to persons skilled in the art of synthetic chemistry. Suitable functional derivatives include acyl halides, anhydrides, and esters. The reaction conditions for mixing (IV) and (V) to produce (I) are well known conditions to the ordinary skilled synthetic chemist.

The compounds of Formula I wherein RI is hydrogen and the substituents in the 3- and 4-positions of the piperidine ring have the trans configuration, said compounds being represented by the Formula (Ia), can be prepared by reacting a 7-oxo-3-azabicyclo[4,1,0]heptane of Formula (VI) with a benzamide of Formula (VII). These compounds can be further alkylated in order to obtain a product wherein $R_1$ is other than hydrogen.

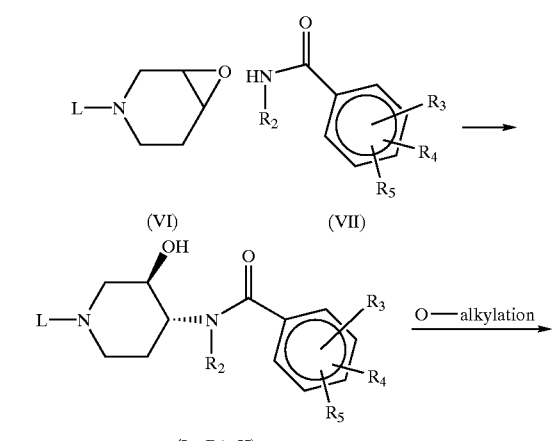

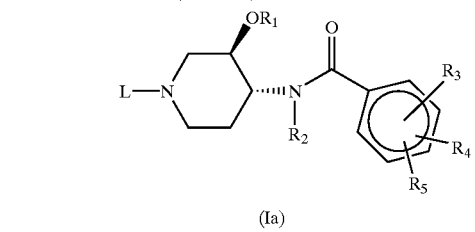

The compounds of Formula (I) wherein the substituents in the 3- and 4-positions of the piperidine ring have the cis configuration, said compounds being represented by the Formula (Ib), can be prepared by the reductive alkylation of a piperidone of Formula (VIII) with a benzamide of Formula (VII). This approach is applicable only when $R_2$ is hydrogen. Another approach, which is applicable whether $R_2$ is hydrogen or lower alkyl, is to react an amine of Formula (IX), having the 3- and 4-substituents of the piperidine ring in the cis configuration, with a carboxylic acid of Formula (V) or a suitable functional derivative thereof (an ester, an anhydride, or an acyl chloride for example).

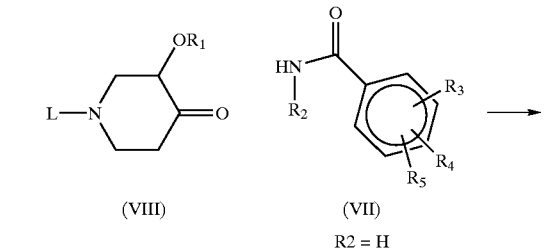

R2 = H

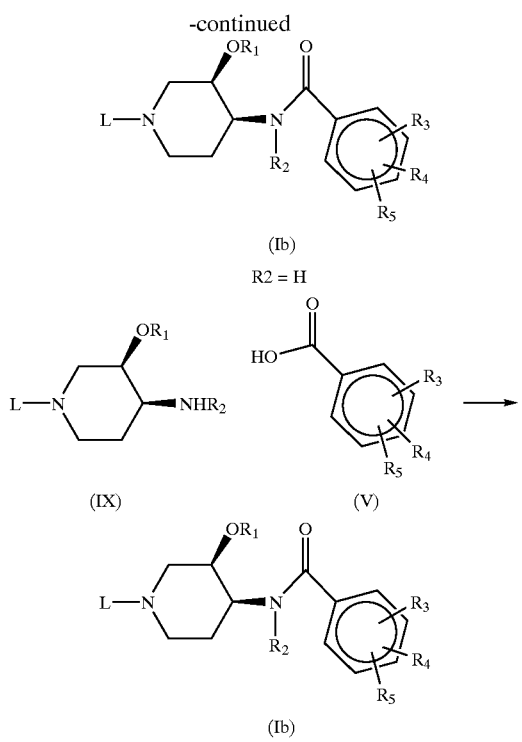

The compounds of this invention have therapeutic properties similar to those of the unmodified parent compounds. Accordingly, dosage rates and routes of administration of the disclosed compounds are similar to those already used in the art and known to the skilled artisan (see, for example, Physicians' Desk Reference, 54th Ed., Medical Economics Company, Montvale, N.J., 2000).

The magnitude of a prophylactic or therapeutic dose of esterified cisapride in the acute or chronic management of diseases and/or disorders described herein will vary with the severity of the condition to be treated, and the route of administration. The dose, and perhaps the dose frequency, will also vary according to the age, body weight, and response of the individual patient. In general, the total daily dose range for esterified cisapride, for the conditions described herein, is from about 1 mg to about 200 mg, in single or divided doses. Preferably, a daily dose range should be between about 5 mg to about 100 mg, in single or divided doses, while most preferably, a daily dose range should be between about 5 mg to about 75 mg, in single or divided doses. It is preferred that the doses are administered from 1 to 4 times a day. In managing the patient, the therapy should be initiated at a lower dose, perhaps about 5 mg to about 10 mg, and increased up to about 50 mg or higher depending on the patient's global response. It is further recommended that children, and patients over 65 years, and those with impaired renal or hepatic function, initially receive low doses, and that they be titrated based on individual response(s) and blood level(s). It may be necessary to use dosages outside these ranges in some cases as will be apparent to those skilled in the art. Further, it is noted that the clinician or treating physician will know how and when to interrupt, adjust, or terminate therapy in conjunction with individual patient response.

The compounds of the subject invention can be formulated according to known methods for preparing pharmaceutically useful compositions. Formulations are described in detail in a number of sources which are well known and readily available to those skilled in the art. For example, Remington's Pharmaceutical Science by E. W. Martin describes formulations which can be used in connection with the subject invention. In general, the compositions of the subject invention are formulated such that an effective amount of the bioactive compound(s) is combined with a suitable carrier in order to facilitate effective administration of the composition.

The compositions of the subject invention include compositions such as suspensions, solutions and elixirs; aerosols; or carriers such as starches, sugars, microcrystalline cellulose, diluents, granulating agents, lubricants, binders, disintegrating agents, and the like, in the case of oral solid preparations (such as powders, capsules, and tablets) with the oral solid preparations being preferred over the oral liquid preparations. A preferred oral solid preparation is capsules. The most preferred oral solid preparation is tablets. Preferred amounts of active ingredient (i.e., an esterified cisapride analog) in a solid dosage form are about 5 mg, 10 mg, and 25 mg.

Further, acceptable carriers can be either solid or liquid. Solid form preparations include powders, tablets, pills, capsules, cachets, suppositories and dispersible granules. A solid carrier can be one or more substances which may act as diluents, flavoring agents, solubilizers, lubricants, suspending agents, binders, preservatives, tablet disintegrating agents or encapsulating materials.

The disclosed pharmaceutical compositions may be subdivided into unit doses containing appropriate quantities of the active component. The unit dosage form can be a packaged preparation, such as packeted tablets, capsules, and powders in paper or plastic containers or in vials or ampules. Also, the unit dosage can be a liquid based preparation or formulated to be incorporated into solid food products, chewing gum, or lozenge.

In addition to the common dosage forms set out above, the compounds of the present invention may also be administered by controlled release means and/or delivery devices such as those described in U.S. Pat. Nos.: 3,845,770; 3,916,899; 3,536,809; 3,598,123; and 4,008,719, the disclosures of which are hereby incorporated by reference in their entirety.

Any suitable route of administration may be employed for providing the patient with an effective dosage of esterified cisapride. For example, oral, rectal, parenteral (subcutaneous, intramuscular, intravenous), transdermal, and like forms of administration may be employed. Dosage forms include tablets, troches, dispersions, suspensions, solutions, capsules, patches, and the like.

One embodiment of the invention provides a method of treating gastroesophageal reflux disease in a mammal, while substantially reducing the concomitant adverse effects associated with the administration of cisapride, which comprises administering to a human in need of such treatment, a therapeutically effective amount of esterified cisapride, or a pharmaceutically acceptable salt thereof. A preferred embodiment is the treatment of gastroesophageal reflux disease in humans.

Another embodiment of the invention provides a composition for the treatment of a human suffering from gastroesophageal reflux disease, which comprises a therapeutically effective amount of esterified cisapride, or a pharmaceutically acceptable salt thereof.

Yet another embodiment of the present invention provides a method of eliciting an anti-emetic effect in a mammal, while substantially reducing the adverse effects associated with the administration of cisapride, which comprises administering to a mammal in need of such anti-emetic therapy, a therapeutically effective amount of esterified cisapride, or a pharmaceutically acceptable salt thereof. Preferably, the mammal is a human.

In an additional embodiment, the present invention encompasses an anti-emetic composition for the treatment of a mammal in need of anti-emetic therapy, which comprises a therapeutically effective amount of esterified cisapride, or a pharmaceutically acceptable salt thereof.

A further aspect of the present invention includes a method of treating a condition caused by gastrointestinal motility dysfunction in a mammal which comprises administering to a mammal in need of treatment for gastrointestinal motility dysfunction, a therapeutically effective amount of esterified cisapride, or a pharmaceutically acceptable salt thereof. Conditions caused by gastrointestinal motility dysfunction include, but are not limited to, dyspepsia, gastroparesis, constipation, post-operative ileus, and intestinal pseudo-obstruction. Preferably, the mammal is a human.

The observation that cisapride enters the central nervous system and binds to 5HT4 receptors indicates that cisapride may have centrally-mediated effects. Cisapride is a potent ligand at 5HT4 receptors, and these receptors are located in several areas of the central nervous system. Modulation of serotonergic systems has a variety of behavioral effects. According, the compounds of the subject invention can be used in the treatment of: 1) cognitive disorders, including but not limited to Alzheimer's disease; 2) behavioral disorders, including but not limited to schizophrenia, mania, obsessive-compulsive disorder, and psychoactive substance use disorders; 3) mood disorders, including but not limited to depression and anxiety; and 4) disorders of control of autonomic function, including but not limited to essential hypertension and sleep disorders.

Accordingly, the present invention also provides methods of treating cognitive, behavioral, mood, or autonomic function control disorders in a mammal comprising the administration of a therapeutically effective amount of esterified cisapride, or a pharmaceutically acceptable salt thereof. Preferably, the mammal is a human.

The term "pharmaceutically acceptable salts" or "a pharmaceutically acceptable salt thereof" refer to salts prepared from pharmaceutically acceptable non-toxic acids or bases including inorganic acids and bases and organic acids and bases. Since the compound of the present invention is basic, salts may be prepared from pharmaceutically acceptable non-toxic acids. Suitable pharmaceutically acceptable acid addition salts for the compound of the present invention include acetic, benzenesulfonic (besylate), benzoic, camphorsulfonic, citric, ethenesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric acid, p-toluenesulfonic, and the like. Preferred acid addition salts are the chloride and sulfate salts. In the most preferred embodiment, esterified cisapride analogs are administered as the free base.

The term "therapeutically effective amount" means: 1) an amount sufficient to alleviate reflux disease, 2) an amount sufficient to alleviate nausea and vomiting, or 3) an amount sufficient to alleviate a condition caused by gastrointestinal motility dysfunction. Therapeutically effective amounts of esterified cisapride are encompassed by the above-described dosage amounts and dose frequency schedule.

A "mammal" may be, for example, a mouse, rat, pig, horse, rabbit, goat, pig, cow, cat, dog, or human. In a preferred embodiment, the mammal is a human.

The term "individual(s)" is defined as a single mammal to which is administered a compound of the present invention. The mammal may be a rodent, for example a mouse or rat, pig, horse, rabbit, goat, pig, cow, cat, dog, or human. In a preferred embodiment, the individual is a human.

The term "esterified cisapride" means therapeutic compounds of the subject invention which contain an ester group which does not detract from the ability of these compounds to provide a therapeutic benefit, but which makes these compounds more susceptible to degradation by hydrolases, particularly serum and/or cytosolic esterases, and which reduces the interaction of the cytochrome P-450 drug detoxification system with the cisapride compounds. Esterase mediated metabolism of the esterified cisapride compounds reduces the role of the cytochrome P-450 drug detoxification system in cisapride metabolism and reduces or eliminates adverse effects caused by cisapride.

The term "adverse effects" includes, but is not limited to, gastrointestinal disorders such as diarrhea, abdominal cramping, and abdominal grumbling; tiredness; headache; increased systolic pressure; death; ventricular tachycardia; ventricular fibrillation; torsades de pointes; QT prolongation; increased heart rate; neurological and CNS disorders; and interaction of cisapride with other drugs given concurrently such as digoxin, diazepam, ethanol, acenocoumarol, cimetidine, ranitidine, paracetamol, and propranolol.

The term "gastroesophageal reflux disease" as used herein means the incidence of, and the symptoms of, those conditions causing the backward flow of the stomach contents into the esophagus.

The terms "eliciting an anti-emetic effect" and "anti-emetic therapy" as used herein mean providing relief from or preventing the symptoms of nausea and vomiting induced spontaneously or associated with emetogenic cancer chemotherapy or irradiation therapy.

The term "treating a condition caused by gastrointestinal motility dysfunction" as used herein means treating the symptoms and conditions associated with this disorder which include, but are not limited to, dyspepsia, gastroparesis, constipation, post-operative ileus, and intestinal pseudo-obstruction.

The term "prokinetic" as used herein means the enhancement of peristalsis in, and thus the movement through the gastrointestinal tract.

The term "dyspepsia" as used herein means a condition characterized by an impairment of the power or function of digestion that can arise as a symptom of a primary gastrointestinal dysfunction or as a complication due to other disorders such as appendicitis, gallbladder disturbances, or malnutrition.

The term "gastroparesis" as used herein means a paralysis of the stomach brought about by a motor abnormality in the stomach or as a complication of diseases such as diabetes, progressive systemic sclerosis, anorexia nervosa, or myotonic dystrophy.

The term "constipation" as used herein means a condition characterized by infrequent or difficult evacuation of feces resulting from conditions such as lack of intestinal muscle tone or intestinal spasticity.

The term "post-operative ileus" as used herein means an obstruction in the intestine due to a disruption in muscle tone following surgery.

The term "intestinal pseudo-obstruction" as used herein means a condition characterized by constipation, colicky pain, and vomiting, but without evidence of physical obstruction.

All patents, patent applications, provisional applications, and publications referred to or cited herein are incorporated by reference in their entirety to the extent they are not inconsistent with the explicit teachings of this specification.

Following is an example which illustrates procedures for practicing the invention. This example should not be construed as limiting. All percentages are by weight and all solvent mixture proportions are by volume unless otherwise noted.

EXAMPLE 1

Synthesis of Specific Compounds of the Subject Invention

Preferred compounds of the subject invention have the Formula (Ib) where the substituents at the 3- and 4-positions of the piperidine ring have the cis-configuration, $R_1$ is methoxy, $R_2$ is hydrogen, $R_4$ is methoxy, $R_5$ is amino, $R_6$ is chloro in the 2-, 4-, and 5-positions of the benzamide ring, respectively. In particularly preferred compounds, L has the Formula (II) wherein n=2, m=0, X is a direct bond, and Y is hydrogen, methyl, ethyl, isopropyl, sec-butyl, or 4-fluorophenyl. The common intermediate to these preferred compounds is compound 9 as described below.

The synthesis can be described in more details as follows:

1-carbethoxy-4-piperidone 1 reacts with bromine in an inert solvent such as dichloromethane to give high yields of 1-carbethoxy-3-bromo-4-piperidone 2. The bromo compound 2 reacts with sodium methoxide in methanol to give 1-carbethoxy-3-hydroxy-4,4-dimethoxypiperidine 3, which in turn is alkylated to the corresponding 3-methoxy analog 4 with iodomethane in dimethylformamide in the presence of sodium hydride. The ketal 4 is hydrolyzed to 1-carbethoxy-3-methoxy-4-piperidone 5 by stirring in 1% sulfuric acid at room temperature. The amine 6 of cis-configuration is then readily obtained by reductive alkylation of 5 with benzylamine in the presence of hydrogen gas and 10% Pd/C with a small amount of thiophene. Further hydrogenolysis of the benzyl moiety with Pd/C and no thiophene gives the primary amine 7. Compound 7 in turn reacts with the commercially available 4-amino-5-chloro-2-methoxybenzoic acid in the presence of DCC and dimethylaminopyridine in dichloromethane to give the benzamide 8. Compound 8 is then hydrolyzed to the intermediate 9 with potassium hydroxide in ethanol/water.

The intermediate 2 reacts with acrylic acid or an ester thereof in the presence of a base such as diethylamine to give the final compounds 11 (see diagram below).

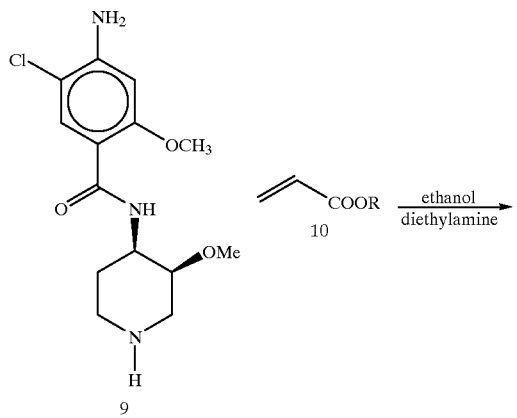

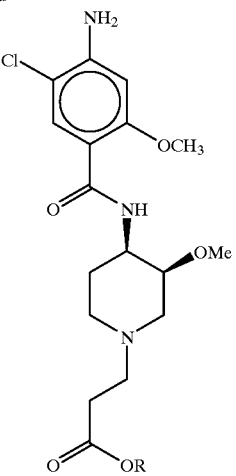

11
R=H, Methyl,ethyl
isopropyl, sec-butyl
4-flourophenyl

For example: Acryloyl chloride and 4-fluorophenol react in dichloromethane in the presence of triethylamine to give 4-fluorophenyl acrylate 10 (R=4-fluorophenyl). Compound 10 is then added to a solution of 9 in ethanol and diethylamine to give 11 (R=4-fluorophenyl) after usual workup.

EXAMPLE 2

Additional Synthesis Protocols

In addition to the general synthetic methods described above, the following procedures can also be utilized:

The compounds of Formula (I) wherein X is oxygen and $R_1$ is methoxy can be prepared by reduction of a compound of Formula (VIII) with sodium borohydride in lower alkanol solvent, followed by coupling of the resulting alcohol (X) with a substituted benzoic acid of Formula (V) in the presence of a coupling reagent such as a dialkylcarbodiimide.

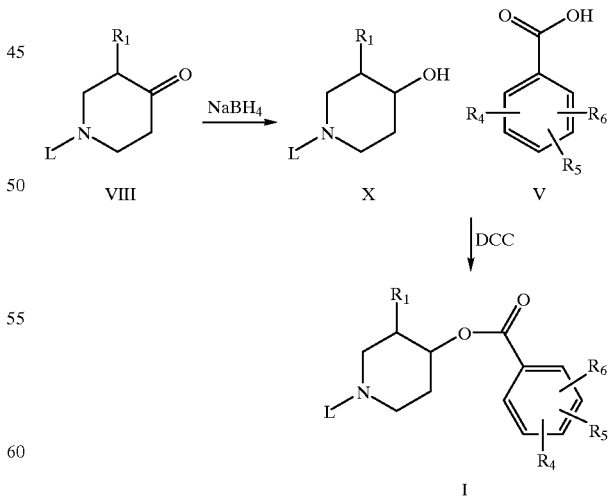

Compounds of Formula I where L is $CH_2CHMeCOOR$ can be prepared by reacting the amine intermediate IX with methacrylic acid or an ester thereof, optionally in the presence of a base such as Triton B or triethylamine.

Compounds of Formula I where L is CH$_2$CMe$_2$COOR can be prepared according to Katritzky et al., Synthesis (1989), 747 by reacting the benzotriazolylmethyl derivative of the amine intermediate IX with a 2-bromoisobutyric acid ester in the presence of zinc and trimethylsilyl chloride.

Compounds of Formula I where L is CH$_2$COOR are prepared by alkylating intermediate IX with bromoacetic acid or an ester thereof in the presence of a base such as potassium carbonate or triethylamine in an inert solvent such as tetrahydrofuran or dimethylformamide.

Compounds of Formula I where L is (CH$_2$)$_3$COOR can be made by alkylating intermediate IX with 4-bromobutyric acid or an ester thereof in the presence of a base such as potassium carbonate or triethylamine in an inert solvent such as tetrahydrofuran or dimethylformamide.

EXAMPLE 3

Additional Synthesis Procedures
3-[4-(4-amino-5-chloro-2-methoxy-benzoylamino)-3-methoxy-piperidin-1-yl]-propionic Acid

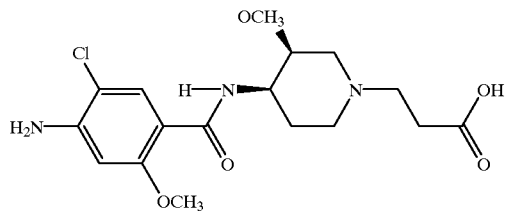

A solution of 4-amino-5-chloro-2-methoxy-N-(3-methoxy-piperidin-4-yl)-benzamide (1 g, 3.2 mmol), and 241 μL of acrylic acid in 50 ml dichloromethane was stirred under nitrogen for 6 hr then concentrated in vacuo. The residue was slurried with hot ethyl acetate and filtered at room temperature to yield 1.15 g of product as a white solid.
Substituting Methacrylic Acid for Acrylic Acid Provided:
3-[4-(4-amino-5-chloro-2-methoxy-benzoylamino)-3-methoxy-piperidin-1-yl]-2-methyl-propionic Acid

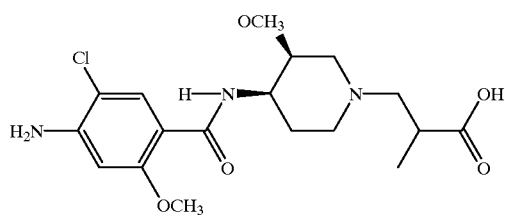

EXAMPLE 4

Additional Synthesis Procedures
3-[4-(4-amino-5-chloro-2-methoxy-benzoylamino)-3-methoxy-piperidin-1-yl]-propionic Acid Methyl Ester

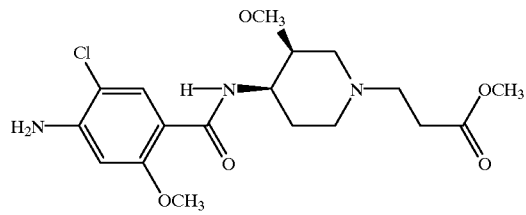

A solution of 640 mg of 3-[4-(4-Amino-5-chloro-2-methoxy-benzoylamino)-3-methoxy-piperidin-1-yl]-propionic acid in 20 ml methanol was treated with 1 ml sulfuric acid and heated at reflux under argon for 3 hr. The mixture was diluted with sodium carbonate solution, extracted into dichloromethane dried over sodium sulfate, and concentrated in vacuo to provide 600 mg of crude ester as an oil. Trituration with methanol/ethyl acetate afforded a crystalline solid.

The following compounds can be similarly prepared:
3-[4-(4-amino-5-chloro-2-methoxy-benzoylamino)-3-methoxy-piperidin-1-yl]-propionic acid ethyl ester
3-[4-(4-amino-5-chloro-2-methoxy-benzoylamino)-3-methoxy-piperidin-1-yl]-propionic acid isopropyl ester
3-[4-(4-amino-5-chloro-2-methoxy-benzoylamino)-3-methoxy-piperidin-1-yl]-propionic acid 2-methoxy-ethyl ester
3-[4-(4-amino-5-chloro-2-methoxy-benzoylamino)-3-methoxy-piperidin-1-yl]-propionic acid cyclohexyl ester
3-[4-(4-amino-5-chloro-2-methoxy-benzoylamino)-3-methoxy-piperidin-1-yl]-2-methyl-propionic acid ethyl ester
3-[4-(4-amino-5-chloro-2-methoxy-benzoylamino)-3-methoxy-piperidin-1-yl]-2-methyl-propionic acid isopropyl ester
3-[4-(4-amino-5-chloro-2-methoxy-benzoylamino)-3-methoxy-piperidin-1-yl]-2-methyl-propionic acid 2-methoxy-ethyl ester
3-[4-(4-amino-5-chloro-2-methoxy-benzoylamino)-3-methoxy-piperidin-1-yl]-2-methyl-propionic acid cyclohexyl ester

EXAMPLE 5

Additional Synthesis Procedure
[4-(4-amino-5-chloro-2-methoxy-benzoylamino)-3-methoxy-piperidin-1-yl]-acetic Acid Methyl Ester

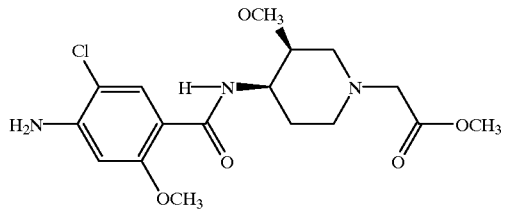

A mixture containing 313 mg norcisapride and 276 mg potassium carbonate in 10 ml DMF was treated with 153 mg of bromo-acetic acid methyl ester. The reaction was stirred at ambient temperature for 8 hr. Extractive workup with water dichloromethane followed by flash chromatography afforded 455 mg of product.

The following compounds can be similarly prepared:
[4-(4-amino-5-chloro-2-methoxy-benzoylamino)-3-methoxy-piperidin-1-yl]-acetic acid phenyl ester
[4-(4-amino-5-chloro-2-methoxy-benzoylamino)-3-methoxy-piperidin-1-yl]-acetic acid 4-fluoro-benzyl ester

EXAMPLE 6

Additional Synthesis Procedures
4-[4-(4-amino-5-chloro-2-methoxy-benzoylamino)-3-methoxy-piperidin-1-yl]-butric Acid Ethyl Ester

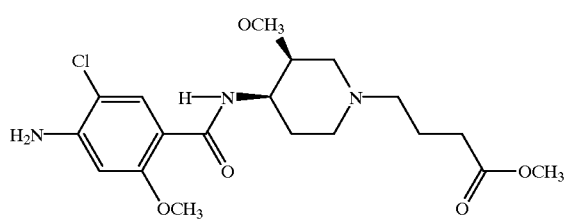

A mixture containing 313 mg norcisapride, 276 mg potassium carbonate, and a pinch of sodium iodide in 10 ml DMF was treated with 195 mg 4-bromo-butyric acid ethyl ester. The reaction was stiffed at ambient temperature for 14 hr. Extractive workup with water/dichloromethane followed by flash chromatography afforded 230 mg of product.

The following compounds can be similarly prepared:

[4-(4-amino-5-chloro-2-methoxy-benzoylamino)-3-methoxy-piperidin-1-yl]-butyric acid phenyl ester

[4-(4-amino-5-chloro-2-methoxy-benzoylamino)-3-methoxy-piperidin-1-yl]-butyric acid 4-fluoro-benzyl ester

EXAMPLE 7

Activity Assay

A segment of oesophagus obtained from Wistar derived male or female rats weighing 270±25 g and sacrificed by $CO_2$ overexposure is used. The tissue is placed under 1 g tension in a 10 mL bath containing 3 $\mu$M indomethacin and 1 $\mu$M ketanserin in Krebs solution pH 7.4 and at 32° C. and submaximal tonic isometrically recorded contraction is induced by carbachol (1 $\mu$M). Test substance (30 $\mu$M)-induced relaxation by 50 percent or more ($\geq$50%) within 5 min, relative to control 0.3 $\mu$M serotonin (5-HT) response, indicates possible receptor agonist activity.

At a test substance concentration where no significant agonist activity is seen, ability to reduce the serotonin-induced relaxatant response by 50 percent or more ($\geq$50%) indicates receptor antagonist activity.

It should be understood that the examples and embodiments described herein are for illustrative purposes only and that various modifications or changes in light thereof will be suggested to persons skilled in the art and are to be included within the spirit and purview of this application and the scope of the appended claims. Further, all patents, patent applications, provisional applications, and publications referred to or cited herein are incorporated by reference in their entirety to the extent they are not inconsistent with the explicit teachings of this specification.

What is claimed is:

1. A method for treating a disease state by stimulating the motility of the gastrointestinal system, and wherein said disease state is selected from the group consisting of gastroesophageal reflux disease, dyspepsia, gastroparesis, constipation, post-operative ileus, and intestinal pseudo-obstruction, wherein said method comprises administering, to an individual in need of such a treatment, a compound, or an analog or salt thereof, wherein said compound has the following structure:

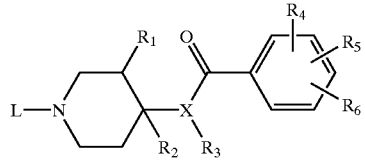

(I)

wherein:

$R_1$ is H, $C_{1-4}$ alkyl, OH, $OC_{1-4}$alkyl, —COOH, —$COOC_{1-4}$alkyl, —O(C=O)$OC_{1-4}$alkyl, —O(C=O)$C_{1-4}$alkyl, or —$C_{1-4}$alkyl$NR_7R_8$ where $R_7$ and $R_8$ are, independently, H or $C_{1-4}$ alkyl;

$R_2$ is H, $C_{1-4}$ alkyl, —$OC_{1-4}$alkyl, —COOH, or —(C=O) $OC_{1-4}$alkyl;

X is O or N;

$R_3$ is H or $C_{1-3}$ alkyl (if X is an oxygen atom, then $R_3$ does not exist);

$R_4$, $R_5$, and $R_6$ are each, independently, selected from the group consisting of hydrogen, $C_{1-4}$ alkyl, —$OC_{1-4}$ alkyl, halogen atom, hydroxy, cyano, nitro, amino, mono- and di(lower alkyl)amino, aminocarbonyl, arylcarbonylamino, alkylcarbonylamino, lower-alkyl carbonyl, lower-alkyl carbonyloxy, aminosulfonyl, lower-alkylsulfinyl, lower-alkylsulfonyl, lower-alkylthio and mercapto; and wherein L has the formula —$C_nH_{2n}$X—$C_mH_{2m}$—(C$R_9$$R_{10}$)$_p$—(C=O)O—Y, wherein n is an integer from 1 to 4 inclusive;

X is —CH(OH)—, —NH—, —S—, —O—, or a direct bond;

m is an integer from 0 to 4 inclusive;

p is 0 or 1;

$R_9$ and $R_{10}$ are, independently, H, $C_{1-4}$ alkyl, or $R_9R_{10}$ are linked and together form a 5- or a 6-membered cycloalkyl ring; and Y is cycloalkyl optionally substituted by 1 or more heteroatoms selected from the group consisting of O; N; S; or aryl or heteroaryl optionally substituted by 1 or more halogen atoms, $C_{1-4}$ alkyl, $C_{1-4}$alkoxy, hydroxy, cyano, amino, alkylamino, dialkylamino, trifluoromethyl, —COOH, or —$COOC_{1-4}$alkyl.

2. The method, according to claim 1, wherein said disease state is selected from the group consisting of gastroesophageal reflux disease, dyspepsia, gastroparesis, constipation, post-operative ileus, and intestinal pseudo-obstruction.

3. The method, according to claim 2, wherein said disease state is gastroesophageal reflux disease.

4. The method, according to claim 1, wherein said individual is a human.

5. The method, according to claim 1, wherein $R_4$, $R_5$, and $R_6$ are, independently, selected from the group consisting of halo, amino, mono- and dialkylamino, and lower alkyloxy.

6. The method, according to claim 1, wherein $R_4$ is methoxy, $R_5$ is amino or methylamino, and $R_6$ is chloro, in the 2-, 4-, and 5-position of the phenyl ring, respectively.

7. The method, according to claim 1, wherein said compound is selected from the group consisting of:

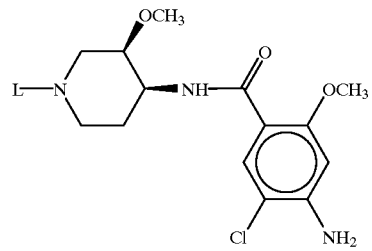

(IIIa)

(IIIb)

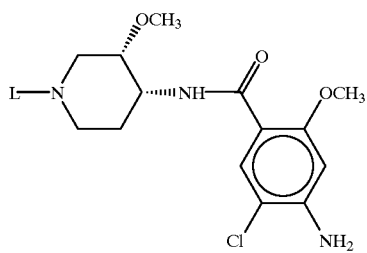

where IIIa and IIIb are mirror images of each other (enantiomers), and where L is defined as shown in Formula (II):

(II)

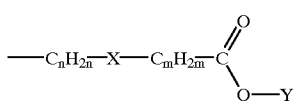

where n=1 to 4, m=0 to 4, X is a direct bond and Y is hydrogen, lower alkyl, or substituted aryl.

8. The method, according to claim 1, wherein $R_1$=OCH$_3$, $R_2$=H; X=O or N (if X=N, then $R_3$=H); $R_4$, $R_5$, and $R_6$ are methoxy, amino, and chlorine at the 2, 4, and 5-position of the phenyl ring, respectively.

9. The method, according to claim 1, wherein both asymmetric centers are in the cis-configuration.

10. A pharmaceutical composition comprising a therapeutically-effective amount of a compound, or a salt thereof, wherein said compound has the following structure:

(I)

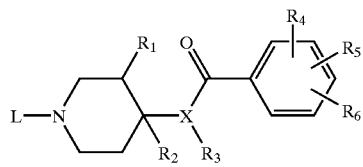

wherein:

$R_1$ is H, $C_{1-4}$ alkyl, OH, OC$_{1-4}$alkyl, —COOH, —COOC$_{1-4}$alkyl, —O(C=O)OC$_{1-4}$alkyl, —O(C=O) C$_{1-4}$alkyl, or —C$_{1-4}$alkylNR$_7$R$_8$ where R$_7$ and R$_8$ are, independently, H or C$_{1-4}$ alkyl;

$R_2$ is H, $C_{1-4}$ alkyl, —OC$_{1-4}$alkyl, —COOH, or —(C=O) OC$_{1-4}$alkyl;

X is O or N;

$R_3$ is H or $C_{1-3}$ alkyl (if X is an oxygen atom, then $R_3$ does not exist);

$R_4$, $R_5$, and $R_6$ are each, independently, selected from the group consisting of hydrogen, $C_{1-4}$ alkyl, —OC$_{1-4}$ alkyl, halogen atom, hydroxy, cyano, nitro, amino, mono- and di(lower alkyl)amino, aminocarbonyl, arylcarbonylamino, alkylcarbonylamino, lower-alkyl carbonyl, lower-alkyl carbonyloxy, aminosulfonyl, lower-alkylsulfinyl, lower-alkylsulfonyl, lower-alkylthio and mercapto; and wherein L has the formula —C$_n$H$_{2n}$—X—C$_m$H$_{2m}$— (CR$_9$R$_{10}$)$_p$—(C=O)O—Y, wherein n is an integer from 1 to 4 inclusive;

X is —CH(OH)—, —NH—, —S—, —O—, or a direct bond;

m is an integer from 0 to 4 inclusive;

p is 0 or 1;

$R_9$ and $R_{10}$ are, independently, H, $C_{1-4}$ alkyl, or $R_9R_{10}$ are linked and together form a 5- or a 6-membered cycloalkyl ring; and Y is cycloalkyl optionally substituted by 1 or more heteroatoms selected from the group consisting of O; N; S; or aryl or heteroaryl optionally substituted by 1 or more halogen atoms, $C_{1-4}$ alkyl, $C_{1-4}$alkoxy, hydroxy, cyano, amino, alkylamino, dialkylamino, trifluoromethyl, —COOH, or —COOC$_{1-4}$alkyl.

11. The pharmaceutical composition, according to claim 10, wherein $R_4$, $R_5$, and $R_6$ are, independently, selected from the group consisting of halo, amino, mono- and dialkylamino, and lower alkyloxy.

12. The pharmaceutical composition, according to claim 10, wherein $R_4$ is methoxy, $R_5$ is amino or methylamino, and $R_6$ is chloro, in the 2-, 4-, and 5-position of the phenyl ring, respectively.

13. The pharmaceutical composition, according to claim 10, wherein said compound is selected from the group consisting of:

(IIIa)

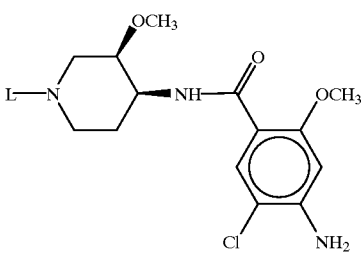

(IIIb)

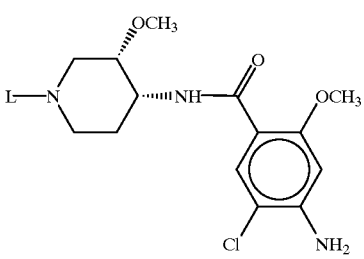

where IIIa and IIIb are mirror images of each other (enantiomers), and where L is defined as shown in Formula (II):

(II)

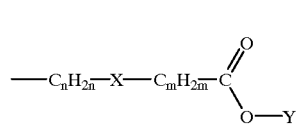

where n=1 to 4, m=0 to 4, X is a direct bond and Y is hydrogen, lower alkyl, or substituted aryl.

14. The pharmaceutical composition, according to claim 10, wherein $R_1$=OCH$_3$, $R_2$=H; X=O or N (if X=N, then $R_3$=H); $R_4$, $R_5$, and $R_6$ are methoxy, amino, and chlorine at the 2, 4, and 5-position of the phenyl ring, respectively.

15. The pharmaceutical composition, according to claim 10, wherein both asymmetric centers are in the cis-configuration.

16. A compound, or salt thereof, wherein said compound has the following structure:

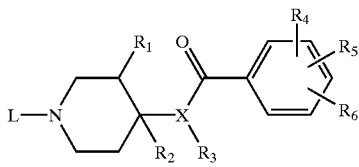

(I)

wherein:

R$_1$ is H, C$_{1-4}$ alkyl, OH, OC$_{1-4}$alkyl, —COOH, —COOC$_{1-4}$alkyl, —O(C═O)OC$_{1-4}$alkyl, —O(C═O)C$_{1-4}$alkyl, or —C$_{1-4}$alkylNR$_7$R$_8$ where R$_7$ and R$_8$ are, independently, H or C$_{1-4}$ alkyl;

R$_2$ is H, C$_{1-4}$ alkyl, —OC$_{1-4}$alkyl, —COOH, or —(C═O)OC$_{1-4}$alkyl;

X is O or N;

R$_3$ is H or C$_{1-3}$ alkyl (if X is an oxygen atom, then R$_3$ does not exist);

R$_4$, R$_5$, and R$_6$ are each, independently, selected from the group consisting of hydrogen, C$_{1-4}$ alkyl, —OC$_{1-4}$ alkyl, halogen atom, hydroxy, cyano, nitro, amino, mono- and di(lower alkyl)amino, aminocarbonyl, arylcarbonylamino, alkylcarbonylamino, lower-alkyl carbonyl, lower-alkyl carbonyloxy, aminosulfonyl, lower-alkylsulfinyl, lower-alkylsulfonyl, lower-alkylthio and mercapto; and wherein L has the formula —C$_n$H$_{2n}$—XC$_m$H$_{2m}$—(CR$_9$R$_{10}$)$_p$—(C═O)O—Y, wherein n is an integer from 1 to 4 inclusive;

X is —CH(OH)—, —NH—, —S—, —O—, or a direct bond;

m is an integer from 0 to 4 inclusive;

p is 0 or 1;

R$_9$ and R$_{10}$ are, independently, H, C$_{1-4}$ alkyl, or R$_9$R$_{10}$ are linked and together form a 5- or a 6-membered cycloalkyl ring; and Y is cycloalkyl optionally substituted by 1 or more heteroatoms selected from the group consisting of O; N; S; or aryl or heteroaryl optionally substituted by 1 or more halogen atoms, C$_{1-4}$ alkyl, C$_{1-4}$alkoxy, hydroxy, cyano, amino, alkylamino, dialkylamino, trifluoromethyl, —COOH, or —COOC$_{1-4}$alkyl.

17. The compound, according to claim 16, wherein R$_4$, R$_5$, and R$_6$ are, independently, selected from the group consisting of halo, amino, mono- and dialkylamino, and lower alkyloxy.

18. The compound, according to claim 16, wherein R$_4$ is methoxy, R$_5$ is amino or methylamino, and R$_6$ is chloro, in the 2-, 4-, and 5-position of the phenyl ring, respectively.

19. The compound, according to claim 16, wherein said compound is selected from the group consisting of:

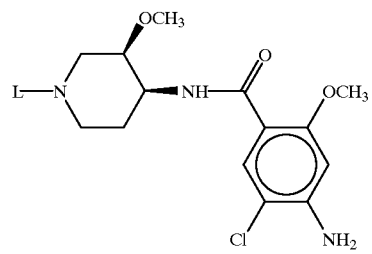

(IIIa)

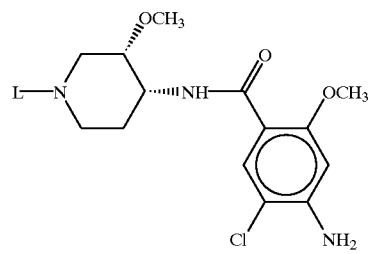

(IIIb)

where IIIa and IIIb are mirror images of each other (enantiomers), and where L is defined as shown in Formula (II):

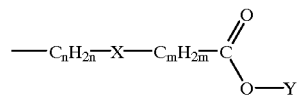

(II)

where n=1 to 4, m=0 to 4, X is a direct bond and Y is hydrogen, lower alkyl, or substituted aryl.

20. The compound, according to claim 16, wherein R$_1$═OCH$_3$, R$_2$═H; X═O or N (if X═N, then R$_3$═H); R$_4$, R$_5$, and R$_6$ are methoxy, amino, and chlorine at the 2, 4, and 5-position of the phenyl ring, respectively.

21. The compound, according to claim 16, wherein both asymmetric centers are in the cis-configuration.

22. A method for treating a condition selected from the group consisting of 1) cognitive disorders, 2) behavioral disorders, 3) mood disorders, and 4) disorders of control of autonomic function wherein said method comprises administering to an individual in need of such treatment, an effective amount of a compound, or an analog or salt thereof, wherein said compound has the following structure:

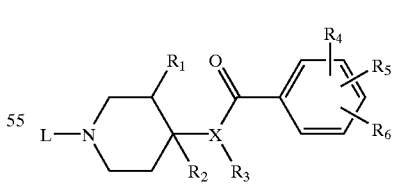

(I)

wherein:

R$_1$ is H, C$_{1-4}$ alkyl, OH, OC$_{1-4}$alkyl, —COOH, —COOC$_{1-4}$alkyl, —O(C═O)OC$_{1-4}$alkyl, —O(C═O)C$_{1-4}$alkyl, or —C$_{1-4}$alkylNR$_7$R$_8$ where R$_7$ and R$_8$ are, independently, H or C$_{1-4}$ alkyl;

R$_2$ is H, C$_{1-4}$ alkyl, —OC$_{1-4}$alkyl, —COOH, or —(C═O)OC$_{1-4}$alkyl;

X is O or N;

$R_3$ is H or $C_{1-3}$ alkyl (if X is an oxygen atom, then $R_3$ does not exist);

$R_4$, $R_5$, and $R_6$ are each, independently, selected from the group consisting of hydrogen, $C_{1-4}$ alkyl, —$OC_{1-4}$ alkyl, halogen atom, hydroxy, cyano, nitro, amino, mono- and di(lower alkyl)amino, aminocarbonyl, arylcarbonylamino, alkylcarbonylamino, lower-alkyl carbonyl, lower-alkyl carbonyloxy, aminosulfonyl, lower-alkylsulfinyl, lower-alkylsulfonyl, lower-alkylthio and mercapto; and wherein L has the formula —$C_nH_{2n}$—X—$C_mH_{2m}$—$(CR_9R_{10})_p$—(C=O)O—Y, wherein n is an integer from 1 to 4 inclusive;

X is —CH(OH)—, —NH—, —S—, —O—, or a direct bond;

m is an integer from 0 to 4 inclusive;

p is 0 or 1;

$R_9$ and $R_{10}$ are, independently, H, $C_{1-4}$ alkyl, or $R_9R_{10}$ are linked and together form a 5- or a 6-membered cycloalkyl ring; and Y is cycloalkyl optionally substituted by 1 or more heteroatoms selected from the group consisting of O; N; S; or aryl or heteroaryl optionally substituted by 1 or more halogen atoms, $C_{1-4}$ alkyl, $C_{1-4}$alkoxy, hydroxy, cyano, amino, alkylamino, dialkylamino, trifluoromethyl, —COOH, or —$COOC_{1-4}$alkyl.

23. The method, according to claim 22, wherein said cognitive disorder is Alzheimer's disease.

24. The method, according to claim 22, wherein said behavioral disorder is selected from the group consisting of schizophrenia, mania, obsessive-compulsive disorder, and psychoactive substance use disorders.

25. The method, according to claim 22, wherein said mood disorder is selected from the group consisting of depression and anxiety.

26. The method, according to claim 22, wherein said mood disorder is selected from the group consisting of depression and anxiety.

27. The method, according to claim 22, wherein said disorder of control of autonomic function is selected from the group consisting of essential hypertension and sleep disorders.

28. The method, according to claim 22, wherein said individual is a human.

29. The method, according to claim 22, wherein $R_4$, $R_5$, and $R_6$ are, independently, selected from the group consisting of halo, amino, mono- and dialkylamino, and lower alkyloxy.

30. The method, according to claim 22, wherein $R_4$ is methoxy, $R_5$ is amino or methylamino, and $R_6$ is chloro, in the 2-, 4-, and 5-position of the phenyl ring, respectively.

31. The method, according to claim 22, wherein said compound is selected from the group consisting of:

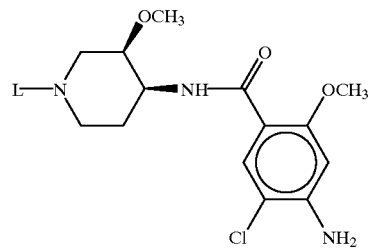

(IIIa)

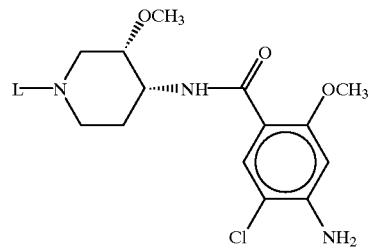

(IIIb)

where IIIa and IIIb are mirror images of each other (enantiomers), and where L is defined as shown in Formula (II):

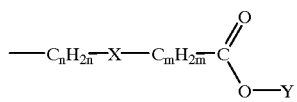

(II)

where n=1 to 4, m=0 to 4, X is a direct bond and Y is hydrogen, lower alkyl, or substituted aryl.

32. The method, according to claim 22, wherein $R_1$=$OCH_3$; $R_2$=H; X=O or N (if X=N, then $R_3$=H); $R_4$, $R_5$, and $R_6$ are methoxy, amino, and chlorine at the 2, 4, and 5-position of the phenyl ring, respectively.

33. The method, according to claim 22, wherein both asymmetric centers are in the cis-configuration.

* * * * *

UNITED STATES PATENT AND TRADEMARK OFFICE
CERTIFICATE OF CORRECTION

PATENT NO.   : 6,552,046 B2
DATED        : April 22, 2003
INVENTOR(S)  : Pascal Druzgala It is certified that error appears in the above-identified patent and that said Letters Patent is hereby corrected as shown below:

Column 13,
Line 47, "...intermediate 2 reacts..." should read -- ...intermediate *9* reacts... --.

Column 22,
Lines 46-47, "...an effective amount..." should read -- ...a therapeutically effective... --.

Signed and Sealed this

Twenty-eighth Day of December, 2004

JON W. DUDAS
*Director of the United States Patent and Trademark Office*